(12) United States Patent
Bashir et al.

(10) Patent No.: US 7,816,100 B2
(45) Date of Patent: *Oct. 19, 2010

(54) APPARATUS AND METHOD FOR DETECTING LIVE CELLS WITH AN INTEGRATED FILTER AND GROWTH DETECTION DEVICE

(75) Inventors: Rashid Bashir, West Lafayette, IN (US); Laila R. Razouk, Sunnyvale, CA (US); Dallas Todd Morisette, Lafayette, IN (US); Bahadir Erimli, Campbell, CA (US)

(73) Assignee: Biovitesse, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/494,213

(22) Filed: Jun. 29, 2009

(65) Prior Publication Data

US 2009/0263856 A1 Oct. 22, 2009

Related U.S. Application Data

(63) Continuation of application No. 12/184,387, filed on Aug. 1, 2008, now Pat. No. 7,553,633, which is a continuation of application No. 10/837,493, filed on Apr. 30, 2004, now Pat. No. 7,413,891.

(60) Provisional application No. 60/467,086, filed on Apr. 30, 2003.

(51) Int. Cl.
*C12Q 1/02* (2006.01)
*C12M 1/34* (2006.01)
*C12M 3/00* (2006.01)

(52) U.S. Cl. .................................... 435/29; 435/287.1

(58) Field of Classification Search ................ 435/29, 435/287.1
See application file for complete search history.

(56) References Cited

U.S. PATENT DOCUMENTS 5,432,086 A   7/1995   Franzl et al.

(Continued)

FOREIGN PATENT DOCUMENTS

| JP | 2002-153297 A | 5/2002 |
| WO | WO00/17630 | 3/2000 |
| WO | WO2004/005922 | 1/2004 |

OTHER PUBLICATIONS

Edmiston et al., "Specificity of a Conductance Assay for Enumeration of *Escherichia coli* from Broiler Carcass Rinse Samples Containing Genetically Similar Species," Journal of Food Protection, 63(2):264-267, 2000.

(Continued)

*Primary Examiner*—Walter D Griffin
*Assistant Examiner*—Lydia Edwards
(74) *Attorney, Agent, or Firm*—Cooley LLP

(57) ABSTRACT

A device for rapid concentration and detection of live cells in fluids includes a filter to capture a cell sample. The filter includes a first physical barrier with apertures of a first size and a second physical barrier with apertures of a second size smaller than the first size to isolate the cell sample on the filter. Growth detection circuitry associated with the filter electrically measures a cell growth rate associated with the cell sample in less than 2 days. The growth detection circuitry includes a mechanical filter for concentration of cells. The filter and growth detection circuitry are integrally formed within the device, which is sealed.

7 Claims, 6 Drawing Sheets

U.S. PATENT DOCUMENTS

| | | | |
|---|---|---|---|
| 5,824,494 | A | 10/1998 | Feldberg |
| 6,143,247 | A | 11/2000 | Sheppard, Jr. et al. |
| 6,280,590 | B1 | 8/2001 | Cheng et al. |
| 6,342,231 | B1 | 1/2002 | Burkhardt et al. |
| 6,468,811 | B1 | 10/2002 | Seul |
| 6,632,656 | B1 | 10/2003 | Thomas et al. |
| 6,716,620 | B2 | 4/2004 | Bashir et al. |
| 6,729,352 | B2 | 5/2004 | O'Connor et al. |
| 6,761,811 | B2 | 7/2004 | Mariella |
| 6,764,583 | B2 | 7/2004 | Miles |
| 6,811,695 | B2 | 11/2004 | Karp |
| 6,818,435 | B2 | 11/2004 | Carvalho et al. |
| 6,919,046 | B2 | 7/2005 | O'Connor et al. |
| 7,306,924 | B2 | 12/2007 | Gomez et al. |
| 7,413,891 | B2 | 8/2008 | Bashir et al. |
| 7,553,633 | B2 * | 6/2009 | Bashir et al. .......... 435/29 |
| 2004/0072278 | A1 | 4/2004 | Chou et al. |
| 2004/0219628 | A1 | 11/2004 | Tashiro et al. |

OTHER PUBLICATIONS

Ehret et al., "Monitoring of Cellular Behaviour by Impedance Measurements on Interdigitated Electrode Structures," Biosensors & Bioelectronics, 12(1):29-41, 1997.

Felice et al., "Impedance of Microbiology: Quantification of Bacterial Content in Milk by Means of Capacitance Growth Curves," Journal of Microbiological Methods, 35:37-42, 1999.

Gomez, et al., "Microfluidic Bochip for Impedance Spectroscopy of Biological Species". Biomedical Micro-Devices, 3(3):201-209, 2001.

Gómez, et al., "Microscale Electronic Detection of Bacterial Metabolism", Sensors and Actuators B, 86:198-208, 2002.

Heller, "An Active Microelectronics Device for Multiplex DNA Analysis", IEEE Engineering in Medicine and Biology, pp. 100-104, 1996.

Li, et al., "Dielectrophoretic Separation and Manipulation of Live and Heat-Treated Cells of Listeria on Microfabricated Devices with Interdigitated Electrodes", Sensors and Actuators B, 86:215-221, 2002.

Vo-Dinh, et al., "Biosensors and Biochips: Advances in Biological and Medical Diagnostics", Fresenius Journal of Analytical Chemistry, 366:540-551, 2000.

Warsinke et al., "Electronic Immunoassays", Fresenius Journal of Analytical Chemistry, 36:622-634, 2000.

Wawerla, et al., "Impedance Microbiology: Applications in Food Hygiene," Journal of Food Protection, 62(12):1488-1496, 1999.

* cited by examiner

APPARATUS AND METHOD FOR DETECTING LIVE CELLS WITH AN INTEGRATED FILTER AND GROWTH DETECTION DEVICE

CROSS REFERENCE TO RELATED APPLICATIONS

This application is a continuation of U.S. patent application Ser. No. 12/184,387 filed Aug. 1, 2008 which is a continuation of U.S. patent application Ser. No. 10/837,493 filed Apr. 30, 2004 which claims the benefit of U.S. Provisional Patent Application No. 60/467,086 filed Apr. 30, 2003, the contents of each are incorporated herein by reference.

BRIEF DESCRIPTION OF THE INVENTION

This invention relates generally to the detection of live cells. More particularly, this invention relates to a method and structure for detecting live cells with a micro-fabricated device with an integrated filter and growth detection circuitry.

BACKGROUND OF THE INVENTION

Micro-fluidics has found increasing use in a wide variety of biomedical applications, including detection and characterization of biological entities. The devices used for such applications are broadly referred to as "biochips". The term biochip has been used in various contexts, but can be generally defined as a micro or nano-fabricated device that is used for processing (e.g., delivery and analysis) of biological entities (e.g., molecules, cells, etc.). This invention relates to the processing of biological entities in the form of cells. As used herein, the term cell broadly refers to any microscopic organism, including bacteria, spores, molds, yeast, plant cells, and animal cells. The invention will be primarily disclosed through the example of bacteria detection. However, it should be appreciated that the invention is generally applicable to the detection of any type of cell.

Biochips based on the impedimetric detection of biological binding events or the amperometric detection of enzymatic reactions exist. Impedimetric detection works by measuring impedance changes produced by the binding of target molecules to receptors (antibodies, for example) immobilized on the surface of microelectrodes. Amperometric devices measure the current generated by electrochemical reactions at the surface of microelectrodes, which are commonly coated with enzymes. Both of these methods can be very sensitive, but preparation of the surfaces of the electrodes (immobilization of antibodies or enzymes) is a complex and sometimes unreliable process, that can be prone to drift and tends to be very sensitive to noise produced by the multitude of species present in real samples (bodily fluids, food, soil, etc.).

A specific example of use of biochips is for the detection of live bacteria and cells from a sample. The very important requirement for the micro-fabricated, impedance-based detection system for this application is the ability to concentrate the small numbers of cells present in the sample being analyzed into the micro-fabricated volume where detection is performed. One prior art approach is to use dielectrophoresis (DEP) to capture immunobeads (microscopic beads coated with charged molecules or antibodies) carrying the cells of interest inside the detection chamber. There are two reasons to use beads. First, the dielectrophoretic force is higher in magnitude on beads in the growth media when compared to the force on cells in the media. Second, the beads could also be used for specific capture of cells.

A key shortcoming associated with existing techniques using biochips for the detection of cells and their growth is that the filtering steps and growth detection steps are separate operations performed on different devices. Various processing operations are currently required to bridge these different operations. For example, a filtering operation performed on the original sample volume of up to a half-liter may use a filter membrane to capture a sample. The filter membrane is then manually moved to a growth area to grow the cells trapped on the membrane. Thus, current filter isolation and transport operations are time consuming and are prone to a variety of errors. In addition, prior art approaches cannot be integrated in an automated way in manufacturing processes where testing of various fluids is performed. It would be highly desirable to eliminate these problems through tightly coupled filtering and cell growth detection operations.

Current methods of bacteria detection almost always involve a growth step wherein the microorganisms are cultured to increase their numbers by several orders of magnitude. Depending on the type of bacteria, this amplification by means of extended growth makes conventional detection methods extremely lengthy, taking anywhere from 2 to 7 days. It would be highly desirable to significantly reduce this amplification stage processing time.

In sum, it would be highly desirable to reduce the amount of time required for cell amplification. Finally, it would be highly desirable to simplify fluidic processing through integrated filtering and cell growth operations.

SUMMARY OF THE INVENTION

A device for rapid concentration and detection of live cells in fluids includes a filter to capture a cell sample. The filter includes a first physical barrier with apertures of a first size and a second physical barrier with apertures of a second size smaller than the first size to isolate the cell sample on the filter. Growth detection circuitry associated with the filter electrically measures a cell growth rate associated with the cell sample in less than 2 days. The growth detection circuitry includes a mechanical filter for concentration of cells. The filter and growth detection circuitry are integrally formed within the device, which is sealed.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

Figure 1:
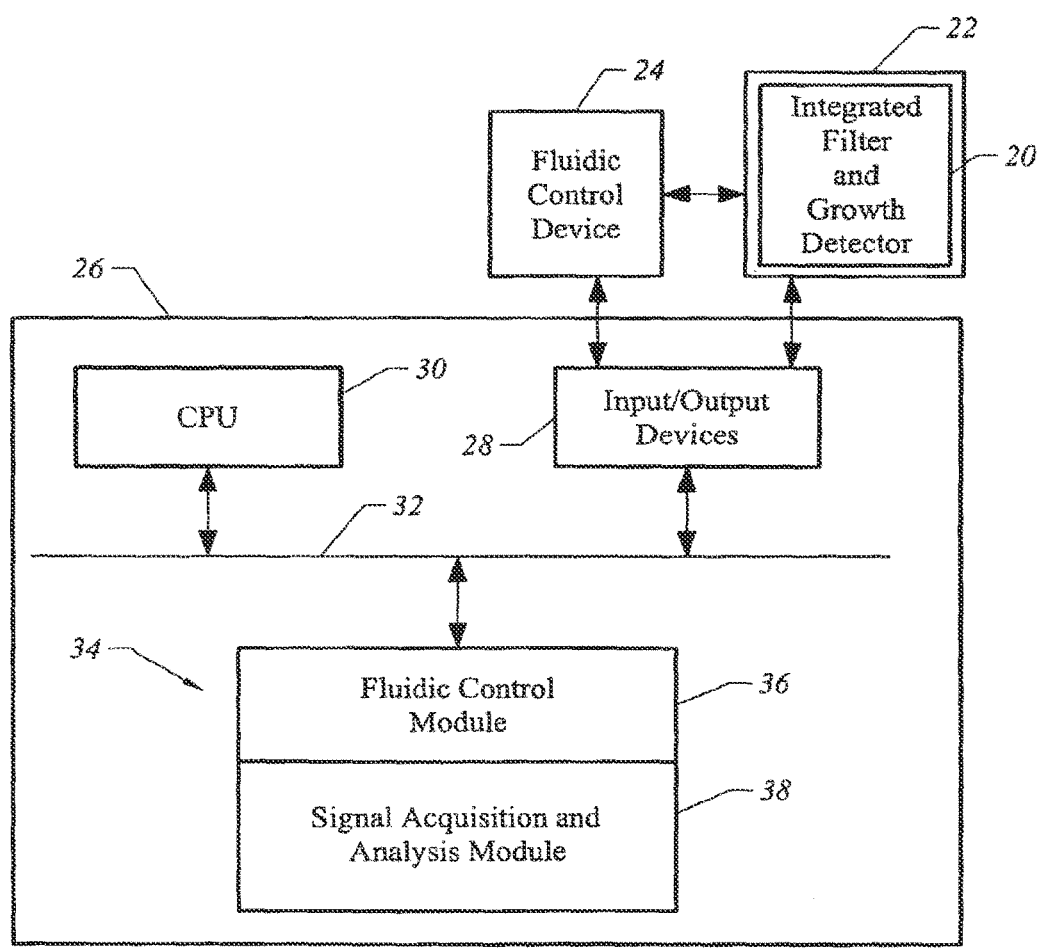
FIG. 1 illustrates an integrated filter and growth detector of the invention as used with a fluidic control device and a computer.

FIG. 1 illustrates an integrated filter and growth detector 20 of the invention that may be used with other components shown in the figure. As will be illustrated, the detector 20 includes one or more micron-scale or nano-scale physical barriers that operate as filters to isolate and capture a cell sample from a fluid. The detector 20 further includes integrated growth detection circuitry to electrically measure a growth rate associated with the captured sample. The integrated filter and growth detector 20 may be a stand-alone device or it maybe positioned within a carrier package 22. In either embodiment, the device is adapted to facilitate handling and interfacing with other physical devices. By way of example, the device may be a plastic package with electrical leads, means to control and maintain temperature for optimal cell growth, and fluid ports. The device may be disposable or reusable.

FIG. 1 further illustrates a fluidic control device 24. The fluidic control device 24 is configured to process fluids and to interface with the integrated filter and growth detector 20, as shown below.

FIG. 1 also illustrates a signal processing and display device (e.g., a computer) 26. In one embodiment, the device 26 includes a set of input and output devices 28 that provide electrical interfaces to the fluidic control device 24 and the integrated filter and growth detector 20. The input and output devices 28 operate under the control of a central processing unit 30, which is linked to the input and output device 28 over a bus 32. A memory 34 is also attached to the bus 32. The memory 34 stores a set of executable programs. In this example, the memory 34 stores an executable program in the form of a fluidic control module 36. The fluidic control module includes executable instructions to control the operation of the fluidic control device 24. Control signals are passed to the fluidic control device 24 through input and output devices 28.

The memory 34 also stores a signal acquisition and analysis module 38. The signal acquisition and analysis module 38 includes a set of executable instructions to process growth rate signals generated by the integrated filter and growth detector 20. In addition, the signal acquisition and analysis module 38 includes executable instructions to control processing on the detector 20. For example, the module 38 controls heating operations performed on the detector 20. In one instance, the module 38 processes an initial device temperature, selects a temperature value, applies a control signal to generate the temperature value on the device, and then monitors the device to maintain the temperature value.

Figure 2:
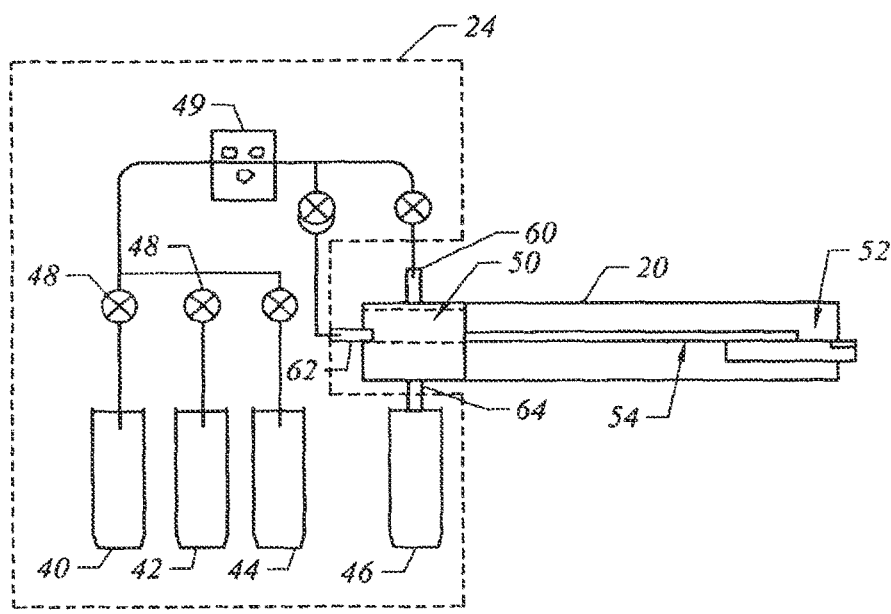
FIG. 2 is a cross-sectional view of the integrated filter and growth detector of the invention coupled to a fluidic control device.

FIG. 2 is a cross-sectional view of a fluidic control device 24 and an integrated filter and growth detector 20 that may be used in accordance with the invention. The fluidic control device 24, in this example, includes a sample reservoir 40, a de-ionized or distilled water reservoir 42, a growth media reservoir 44, and a waste reservoir 46. A pump 49 is used to transport the fluids, while valves 48 are used to control the fluid flow.

As shown in FIG. 2, the integrated filter and growth detector 20 is adapted to interface with the fluidic control device 24. In this embodiment, the detector 20 includes a filter end 50 and a growth detector end 52 connected by a channel 54. The filter end 50 has a first input port 60, a second input port 62, and an output port 64.

Figure 3:
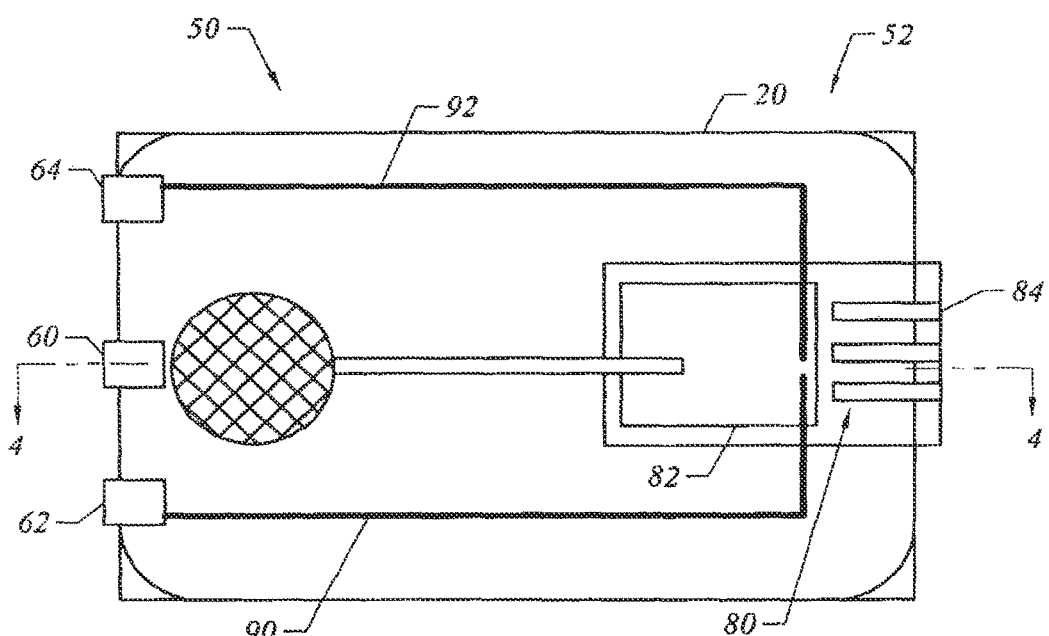
FIG. 3 is a top view of an integrated filter and growth detector configured in accordance with an embodiment of the invention.

FIG. 3 is a top view of an integrated filter and growth detector 20 configured in accordance with an embodiment of the invention. The detector 20 includes a filter end 50 and a growth detector end 52 connected by a channel 54. The filter end 50 includes a filter 70, while the growth detector end 52 includes a base 80. The base 80 (e.g., a printed circuit board) has a metal heater with associated temperature control circuitry (e.g., a sensor). The base 80 also has a separate set of metal electrodes for sensing bacterial growth rate signals generated in measurement chamber 82. The bacterial growth rate signals are routed to an external device, such as computer 26 through electrodes 84.

FIG. 3 illustrates an input port 60, which may be used to inject a fluidic sample of interest, such as growth media. FIG. 3 also illustrates an input port 62, which may be used for pumping operations and an output port 64, which may be used to pass waste fluids. A channel 90 links input port 62 to the measurement chamber 82, while another channel 92 links the output port 64 to the measurement chamber 82.

Figure 4:
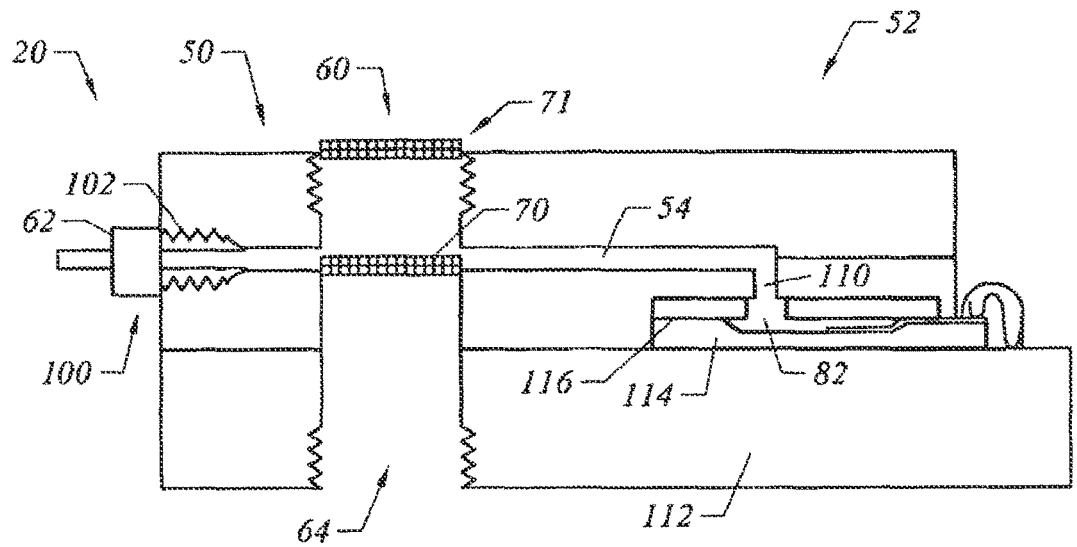
FIG. 4 is a cross-section view of the integrated filter and growth detector of FIG. 3 taken along the line 4-4.

In this example, the detector 20 is a plastic cartridge for disposable use. The filter 70 may be formed within the plastic cartridge body. The filter may be polycarbonate or another plastic material. The growth detector end 52 may include a silicon-fabricated device forming the measurement chamber 82 and required electrical leads. FIG. 4 is a cross-sectional view taken along the line 4-4 of FIG. 3.

FIG. 4 illustrates the filter end 50 and growth detector end 52 of the device. The filter end 50 includes an input port 60, an input port 62, and an output port 64. FIG. 4 illustrates a seal 60 and a threaded member 102 to connect to the device 20. The figure also illustrates filter 70, plus an additional filter 71. The figure also illustrates the previously discussed channel 54, which has an outlet 110 to deliver a fluid to measurement chamber 82. In this example, the diameter of the outlet 110 is 150 μm. The growth detector end 52 also includes a metal heater 112, a silicon substrate 114 and a glass or quartz cover 114. These components maybe mounted on a printed circuit board. Standard semiconductor processing techniques are used to form a cavity in the silicon substrate 114, which serves to operate as a measurement chamber. Similarly, standard semiconductor processing techniques are used to form a heater, a temperature sensor, leads and electrodes to measure a growth rate signal.

In one instance, the device of FIGS. 3-4 is used to concentrate a 100 ml sample, recover the bacteria from the filter 70 and move the bacteria to the measurement chamber 82. The bacteria may be further concentrated in the measurement chamber 82 using a combination of dielectrophoresis, a mechanical filter, or anti-bodies/proteins. The bacteria may also be provided with growth media to facilitate rapid growth. While the bacteria are heated and grown, the growth is detected electronically. In one embodiment impedance changes over time are used to detect the growth.

Figure 5:
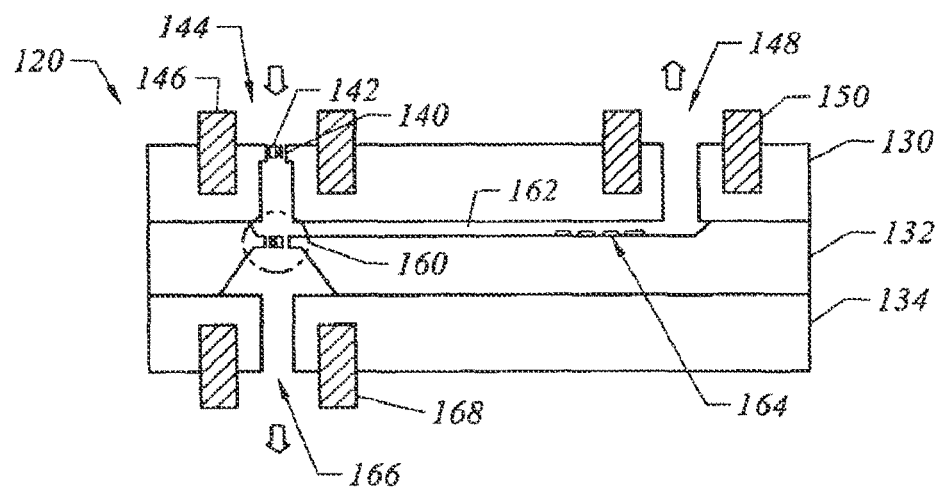
FIG. 5 is a cross-sectional view of an alternate embodiment of an integrated filter and growth detector of the invention.

FIG. 5 illustrates an alternate embodiment of the integrated filter and growth detector of the invention. The detector 120 of FIG. 5 is formed from a stack of semiconductor wafers, including a first wafer 130, a second wafer 132, and a third wafer 134. A first mechanical filter 140 is formed in the first wafer 130. The first mechanical filter 140 comprises a set of apertures 142 etched into the first wafer 130. While only a small number of apertures are shown in FIG. 5, it should be appreciated that there will typically be a large number of apertures etched into the wafer. The first mechanical filter 140 is positioned at a first input port 144 formed by tube 146. The first wafer 130 also includes a first output port 148, surrounded by a tube 150.

FIG. 5 also includes a second wafer 132. The second wafer 132 includes a second mechanical filter 160. The apertures of the second mechanical filter 160 are smaller than those formed in the first mechanical filter 142. By way of example, the first mechanical filter 142 has pore sizes between approximately 2 and 12 µm, preferably between approximately 4 and 8 µm, to trap particles larger than bacteria. The second mechanical filter 160 has pore sizes of approximately 0.2 µm or less to trap bacteria. The thickness of each filter and the percent area of pores is a function of the desired flow rate and the pressure that the membrane can withstand. The second wafer 132 also defines a channel 162. Electrodes 164 are formed in the channel 162 for impedance measurements. The third wafer 134 shown in FIG. 5 includes a second output port 166. A tube 168 is formed around the output port 166.

The device of FIG. 5 may be operated as follows. Fluid is passed through the first input port 144 and is released from the second output port 166, while the first output port 148 is sealed. This traps bacteria on filter 160. The second output port 166 is then sealed. A pulling force is then generated at the first output port 148, which causes the bacteria on filter 160 to flow towards the electrodes 164. During this operation, voltages may be applied to the electrodes 164 to divert bacteria into smaller chambers for measurements. Growth media is flowed into the device, the ports 144, 148, and 166 are then sealed, the bacteria are heated and impedance measurements are taken.

There are some additional observations to be made with respect to the device of FIG. 5. The semiconductor surfaces should be oxidized to passivate the silicon surface and to derivatize the surfaces with proteins and bio-molecules as needed. The height-to-width aspect ratio of the pores is preferably as high as possible, for the purpose of mechanical strength to withstand relatively high-pressure flows. This may be achieved by using DRIE semiconductor processing techniques.

The pore sizes in any of the bacteria trapping filters of the invention are 0.2 µm or less. The pore sizes of the pre-filters are preferably in the range of 4-8 µm. This sizing allows bacteria to pass, while trapping other particles, debris, and cells.

Figure 6:
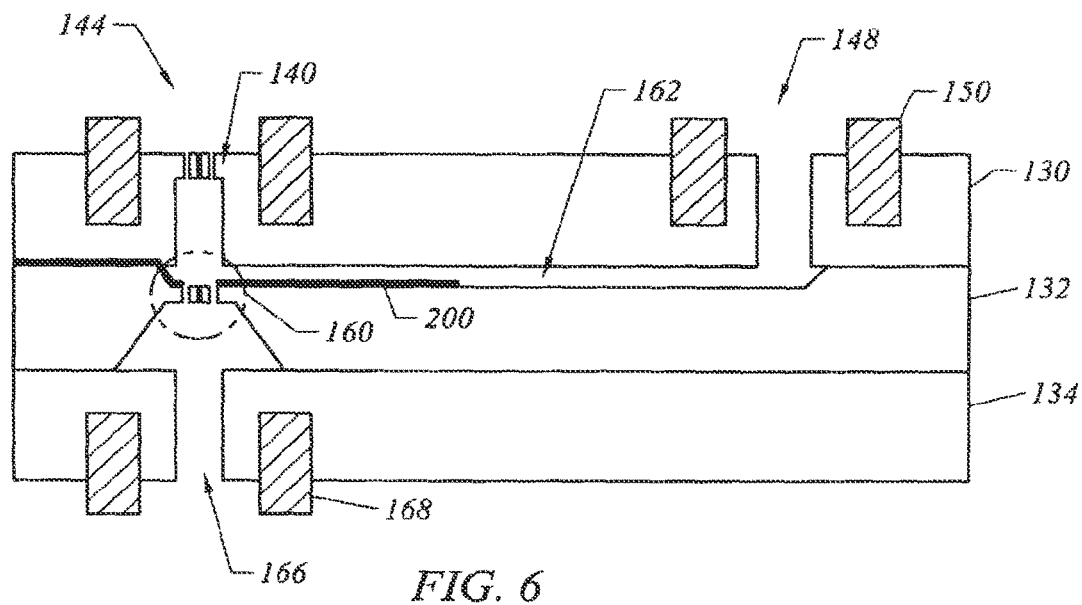
FIG. 6 is a cross-sectional view of another embodiment of an integrated filter and growth detector configured in accordance with an embodiment of the invention.

FIG. 6 illustrates an alternate configuration of the device of FIG. 5. In this embodiment, the electrodes 200 for impedance measurement are immediately adjacent to the second mechanical filter 160. Thus, a bacteria transport operation is not required. The surface of the second mechanical filter 160 may be treated to capture a selected antibody. Fluid is initially pushed through port 144 and is pulled through output port 166, while output port 148 is sealed. This results in bacteria being trapped on filter 160. Output port 166 is then closed and output 148 is opened to create a pulling force, which removes the bacteria, except from the selected antibody. Once the unwanted bacteria are removed, the selected bacteria will remain. Growth media is applied to the device and a heating operation is commenced. Thereafter, impedance measurements are taken.

Figure 7:
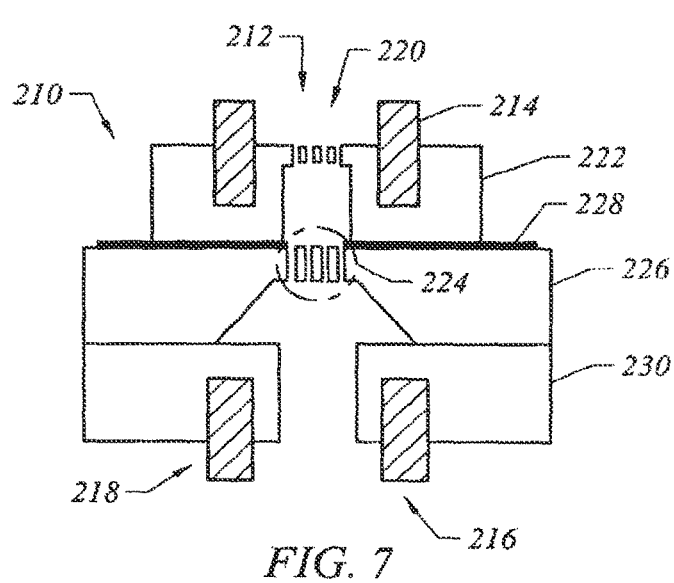
FIG. 7 is a cross-sectional view of another embodiment of an integrated filter and growth detector configured in accordance with an embodiment of the invention.

FIG. 7 illustrates another integrated filter and growth detector 210 configured in accordance with another embodiment of the invention. The detector 210 of FIG. 7 includes a single input port 212 surrounded by a tube 214 and a single output port 216 surrounded by a tube 218. A first mechanic filter 220 is formed in a first wafer 222. A second mechanical filter 224 is formed in a second wafer 226. Electrodes 228 are also formed on the second wafer 226. The output port 216 is formed in a third wafer 230.

Observe that this highly integrated device has only two fluid ports. The electrodes 228 can be built on top of the filter 224 and etched such that the metal is aligned to the apertures of the filter. In this embodiment, bacteria are captured on the filter 224 and measurements are performed without moving the bacteria.

Figure 8:
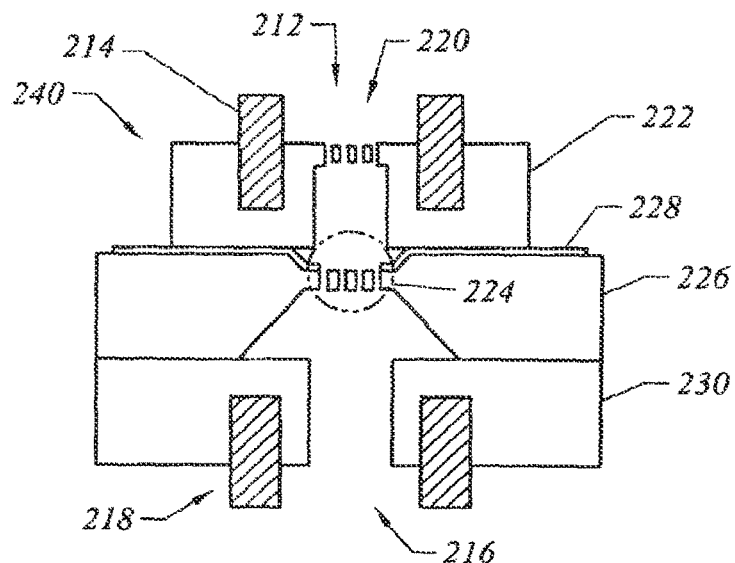
FIG. 8 is a cross-sectional view of another embodiment of an integrated filter and growth detector configured in accordance with an embodiment of the invention.

The device of FIG. 8 generally corresponds to the device of FIG. 7, but in this embodiment the electrodes 228 are formed on the sidewall immediately adjacent to the filter 224. The devices of FIGS. 6-8 may be fabricated to include two types of electrodes: electrodes for DEP concentration and electrodes for impedance measurements. These devices may also include separate heating and heating control devices.

Figure 9:
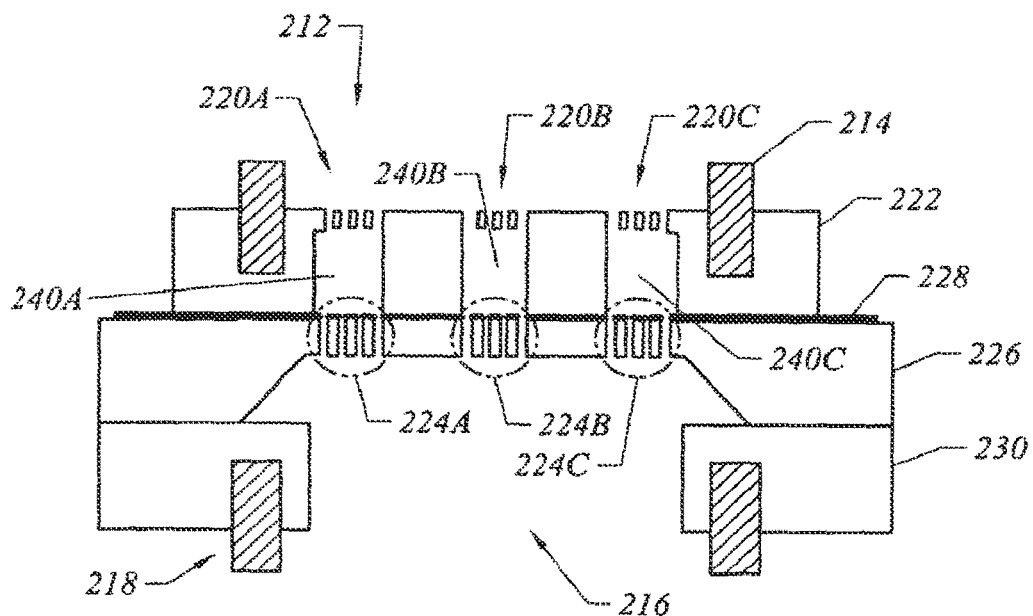
FIG. 9 is a cross-sectional view of a multi-chamber integrated filter and growth detector configured in accordance with an embodiment of the invention.

FIG. 9 generally corresponds to the device of FIG. 7, but in this embodiment a set of first filters 220A, 220B, 220C is provided along with a corresponding set of second filters 224A, 224B, 224C. This configuration facilitates a higher flow rate, but individual chambers 240A, 240B, 240C provide electrical viability detection for smaller volumes to provide a low threshold and time to result for detection. With this embodiment, the various chambers 204A, 240B, 240C can be scanned and impedance measurements can be performed sequentially in various chambers.

Figure 10:
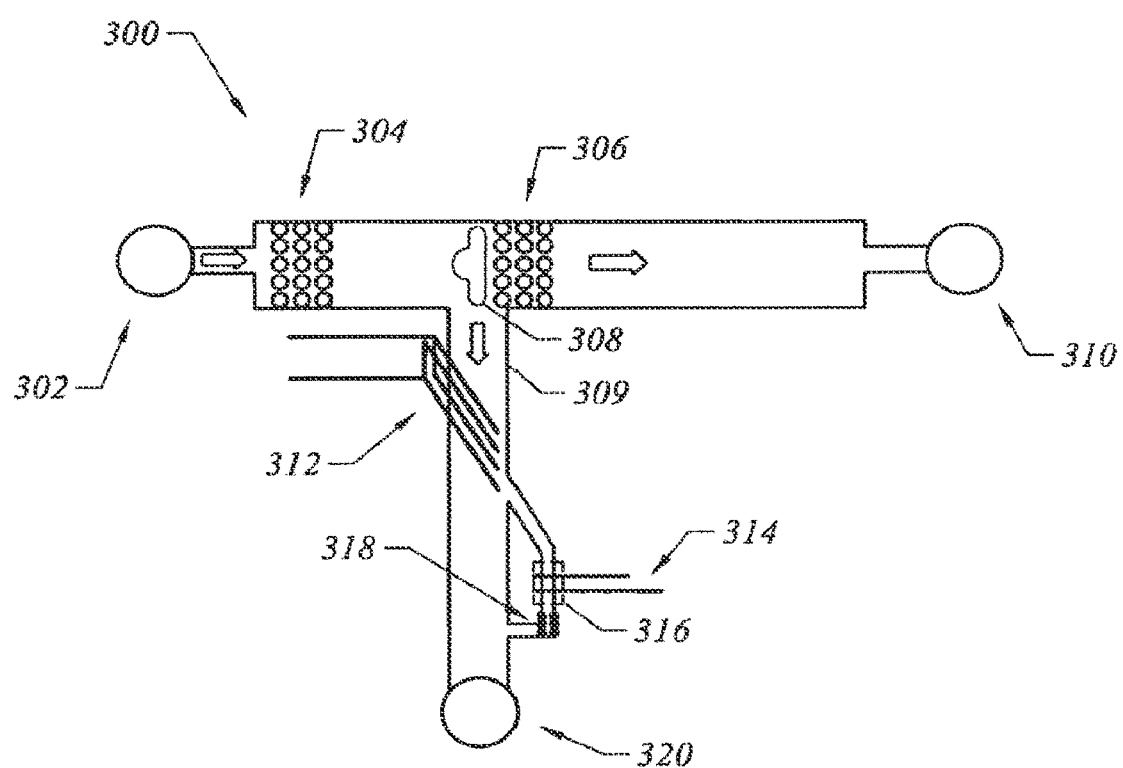
FIG. 10 is a top view of another embodiment of an integrated filter and growth detector configured in accordance with an embodiment of the invention.

FIG. 10 illustrates still another embodiment of the invention. This embodiment utilizes vertically aligned filters (i.e., filters aligned vertically or laterally). Observe that prior embodiments of the invention utilized filters that were horizontally aligned (i.e., aligned in horizontal planes). The device 300 of FIG. 10 includes an input port, a first filter 304 and a second filter 306. In this embodiment, vertically etched pillars form a filter grid or physical barrier. Captured bacteria 308 are routed through a channel 309, which includes electrodes 312 for dielectrophoresis. The dielectrophoresis electrodes 312 route the bacteria to a measurement chamber 316, which includes electrodes 314 for impedance measurements. The movement of the bacteria is dictated by control of the input port 302, the output port 310 and the output port 320.

Fluid is pushed through input 302 and is pulled through output 310, while output 320 is sealed. This traps the bacteria 308 on filter 306. Voltages applied to the electrodes 312 divert bacteria into the smaller measurement chamber 316. In the measurement chamber 316, additional electrodes can be used to stop the bacteria migration. The valves 318 can then be used to isolate the measurement chamber 316.

Observe that embodiments of the invention include: (1) a filtration or concentration operation; (2) a DEP concentration operation; and (3) a growth (e.g., heating with temperature control) and detection operation. The filtration operation can be performed in a non-silicon device (e.g., plastic, as shown in FIG. 4). The DEP concentration operation along with the growth and detection operations may be performed on a silicon-based device, also shown in FIG. 4. Alternately, all of these operations may be performed on a silicon-based device, as shown in FIGS. 5-9. As shown in FIG. 10, the DEP concentration operation may be separate from the growth and detection operation. The advantage of this embodiment is that only the measurement chamber 316 needs to be at a micron or nano-scale. For example, in this embodiment, the electrodes 314 may have a pitch of 10-20 µm and be formed in silicon, while the electrodes 312 may have a pitch of 20-100 µm and be fabricated in plastic. This embodiment is cost-effective since it reduces the silicon die size.

Those skilled in the art will appreciate that there are any number of process flows that may be utilized in accordance with the invention. In general, a fluidic sample will be secured and standard off-chip concentration operations will be performed. These operations, in general, will take approximately 30 minutes. Flow processing and sample concentration is then performed on the chip. This typically takes approximately 45 minutes. Finally, a growth media is injected into the chip and cell detection is initiated. This process typically takes 2-3 hours, a vast improvement over the prior art requirement of many days.

In order to block bacteria in a relatively large flow, it is desirable to reduce the conductivity of the flow medium. De-ionized or distilled water may be used for this purpose. The dielectrophoretic force on cells is much higher in de-ionized or distilled water than in growth media. After cells in a sample have been captured in water, the growth media is injected into the chip to replace the water in the channels, while holding the captured cells using dielectrophoresis. After the water has been flushed out and all the channels are filled with the growth media, the chip is sealed and the incubation and impedance measurement process is started. Replacing the water in the channels by media is essential because water does not provide any of the nutrients the cells need to survive and multiply and without multiplication the metabolic signal is too small to be detected.

Observe that the highly integrated device of the invention obviates the prior art use of multiple devices. This eliminates manual processing operations, which are time-consuming and error prone. In addition, the devices and methods of the invention facilitate automated manufacturing processes. Furthermore, the tightly coupled and highly efficient filtration, concentration, growth and detection operations reduce processing time. Therefore, the invention can be exploited in a variety of new applications. Major markets include human clinical applications, industrial applications, veterinary applications, and homeland security applications. The human clinical market is huge, with bacterial testing being performed on virtually all patients. Industrial microbiological testing is mostly performed in a production environment in four major segments: pharmaceutical and bio-pharmaceutical applications, food applications, environment applications, and beverage applications. Homeland security is an emerging market that has overlap with the other markets and will consist of testing of samples from air, water, food supply, and the like for pathogens. The disclosed invention has wide applications in all of these markets. A discussion of exemplary applications of the invention follows.

An example where rapid detection of growth of any bacteria is critical is in biopharmaceutical manufacturing facilities. In these facilities, there are many instances where a product is held for many days for bacterial viability test results or in some cases the product is moved on through additional steps without getting the results. If the results are negative, then weeks or months of expensive processing is wasted. The reason for this is that these facilities are designed and constructed to hold large volumes of media, buffer, and product while they are stored, waiting for bacterial viability test results. Hence, the rapid bacterial viability test afforded by the present invention can facilitate a change in the way that pharmaceutical manufacturing is performed.

Microbiological control in this segment focuses on the manufacturing environment in order to guarantee control of contamination risks and the quality of finished products. Today, the detection and the identification of bacterial contamination depend largely on conventional culturing techniques that require several days. Furthermore, today's tracking process still relies mostly on human beings recording results in logbooks. It may take up to 10 days to alert the industrial flow to quality control problems.

In addition, in all biopharmaceutical manufacturing, a regularly scheduled repair and maintenance shutdown is usually performed twice a year. For each shutdown, a 7 to 10 day wait period is usually scheduled to obtain the result of bacterial contamination. The fast time to result solution of the invention can save up to 15 days per year. This is equivalent to a yearly saving of $7.5 million for a manufacturing facility requiring $150 million to operate per year.

The invention can also be used in connection with a variety of medical applications. For example, blood and cerebrospinal fluid should be sterile, i.e., have no bacteria. If an infant displays hypothermia and temperature instability, then a culture of the cerebrospinal fluid, called a spinal tap, is performed. Cerebrospinal fluid bathes the brain and the spinal cord and provides nutrients to these vital organs. Neonatal meningitis, a possible outcome of neonatal sepsis, occurs in 2-4 cases per 10,000 live births and significantly contributes to the mortality rate in neonatal sepsis; it is responsible for 4% of all neonatal deaths. One milliliter or less of cerebrospinal fluid is extracted and sent for culture. Meningitis can be due to a virus or bacteria. In the case of bacterial infection of the cerebrospinal fluid, early results from a culture can eliminate unneeded medications and their side effects when meningitis is not present.

In the US alone, the incidence of culture-proven sepsis is approximately 2 in 1000 live births. Approximately 5% of evaluated neonates have culture-proven sepsis. The early signs of sepsis in a newborn are nonspecific; therefore, many newborns undergo diagnostic studies and the initiation of treatment before the diagnosis has been determined. Medical communities like the American Academy of Pediatrics (AAP), American Academy of Obstetrics and Gynecology (AAOG), and Centers for Disease Control and Prevention (CDC) have recommended sepsis screening and/or treatment for various risk factors. Cultures of blood and body fluids may take several days for the organism to grow and be identified. Because of this, babies who are at increased risk for sepsis, such as premature or low birth-weight babies may have preventive medication treatment started as soon as cultures are taken. Because the mortality rate of untreated sepsis can be as high as 50%, most clinicians believe that the hazard of untreated sepsis is too great to wait for confirmation by positive cultures; therefore, most clinicians initiate treatment while waiting for culture results. The treatments, which in most cases are unnecessary, can have side effects, and also are very expensive.

The mortality rate in neonatal sepsis can be as high as 50% for infants who are not treated. Thus, in this specific and critical application of neonatal blood sepsis and cerebrospinal fluid culture, rapid time to result is specifically of interest. Rapid detection of growth of any microorganisms can have a huge impact on the way neonatal medicine is practiced in the intensive care unit. Thus, the technology of the invention facilitates saving lives and reduced treatment costs.

Another application of the invention is for the identification of bacterial contamination of transfused blood platelets. Bacterial contamination of platelets is the leading cause of morbidity and mortality from a transfusion-transmitted infection. It is estimated that as many as one in 4,000 transfusions leads to a severe septic reaction and as many as one in 12,000 transfusions can lead to death due to bacterial contamination. Platelets are the blood component most vulnerable to bacterial contamination because they must be stored at room temperature, which facilitates bacterial growth. Detection is complicated by the fact that there are numerous strains of bacteria with varying growth rates and time needed for some strains to proliferate to the point where they can be detected. A reliable method must be able to detect the most common and lethal bacteria that contaminate platelets prior to platelet outdating, which is only five days in the U.S. The frequency of bacterial contamination of blood platelets and the incidence of illness and fatalities caused by bacterial contamination, greatly exceed that of viruses. Bacterial contamination can be a problem in most blood products; however, since platelets are stored at room temperature they constitute the greatest risk. Thus, the transfusion of a contaminated platelet product is one of the major causes of death for patients that have received a transfusion.

Detection of bacteria in platelets is difficult, mainly due to the very low initial inoculum present in the product. In addition, platelets may be contaminated with a range of bacteria that will grow at different rates. This makes sampling a major challenge to developers and users of test systems, and may cause the presence of bacteria in a product to be missed due to sampling error. Another challenge is the short shelf life of platelets (5-7 days). It is therefore very important to have a rapid and reliable method. Current methods may take days before a positive result is obtained, leaving very little shelf life for the products. When results can be obtained in a few hours, as is the case with the present invention, the transfusion can be performed much earlier from a source of supply, thus reducing the possibility of additional contamination.

As noted earlier, the invention is disclosed in the context of detecting bacterial cells, but the disclosed device and the techniques are equally applicable to other types of cells, such as yeasts, molds, and live mammalian cells.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

What is claimed is:

1. A device for rapid concentration and detection of live cells in fluids, comprising:
    a filter to capture a cell sample, said filter including a physical barrier with apertures to isolate said cell sample on said filter; and
    growth detection circuitry associated with said filter, said growth detection circuitry electrically measuring a cell growth rate associated with said cell sample in less than 2 days;
    wherein said growth detection circuitry includes a mechanical filter for concentration of cells;
    wherein said filter and growth detection circuitry are integrally formed within the device, which is sealed.

2. The device of claim 1 wherein said physical barrier apertures have a diameter of approximately 0.2 µm or less.

3. The device of claim 1 wherein said growth detection circuitry includes a heater, a temperature detector, and a sensor.

4. The device of claim 1 further comprising a channel between said filter and said growth detection circuitry.

5. A method of rapid concentration and detection of cells in fluids, comprising:
    capturing a cell sample within a fluid with a filter including a physical barrier with apertures to isolate said cell sample on said filter;
    routing said cell sample to growth detection circuitry including a mechanical filter for concentration of cells;
    heating said cell sample; and
    measuring a growth rate signal associated with said cell sample, wherein capturing, routing, heating and measuring are performed in a sealed device with micro-scale dimensions and wherein measuring is accomplished in less than 2 days.

6. The method of claim 5 wherein said physical barrier apertures have a diameter of approximately 0.2 µm or less.

7. The method of claim 5 wherein said growth detection circuitry includes a heater, a temperature detector, and a sensor.

* * * * *